United States Patent [19]

Imai

[11] 4,269,998

[45] May 26, 1981

[54] PRODUCTION OF DIALKYL FORMAMIDE

[75] Inventor: Tamotsu Imai, Mt. Prospect, Ill.

[73] Assignee: UOP Inc., Des Plaines, Ill.

[21] Appl. No.: 122,153

[22] Filed: Feb. 19, 1980

[51] Int. Cl.$^3$ ............................................. C07C 102/00
[52] U.S. Cl. ..................................... 564/132; 252/404
[58] Field of Search ..................... 260/561 R; 564/132

[56] References Cited

U.S. PATENT DOCUMENTS

| | | | |
|---|---|---|---|
| 3,530,182 | 9/1970 | Haynes et al. | 260/561 R |
| 3,732,329 | 5/1973 | Thatcher et al. | 585/275 |
| 3,855,347 | 12/1974 | Oricchio | 585/642 |
| 4,019,975 | 4/1977 | Urquhart | 208/10 |

Primary Examiner—Arthur P. Demers
Attorney, Agent, or Firm—James R. Hoatson, Jr.; Raymond H. Nelson; William H. Page, II

[57] ABSTRACT

Dialkyl formamides may be prepared by treating the corresponding dialkyl amine with carbon dioxide and hydrogen in the presence of a transition metal hydrogenation catalyst at a temperature in the range of from about 100° to about 400° C. and a pressure in the range of from about 5 to about 300 atmospheres. The reaction is exemplified by treating dialkyl amine with carbon dioxide and water in the presence of a copper chromite to form N,N-dimethylformamide.

15 Claims, No Drawings

PRODUCTION OF DIALKYL FORMAMIDE

This invention relates to a process for the production of dialkyl formamides. More specifically, the invention is concerned with a process for treating a dialkyl amine with carbon dioxide and hydrogen in the presence of certain catalytic compositions of matter to form the corresponding dialkyl formamide.

Dialkyl formamides which are formed from the corresponding dialkyl amines according to the process of this invention will find a wide variety of uses in the chemical industry. As a specific example of this, N,N-dimethylformamide which is a water-white, non-corrosive liquid, is miscible with water and many organic solvents. This compound may be used as a solvent for vinyl resins, acetylene, butadiene, acid gases, some petroleum components, and due to its miscibility with many inorganic liquids it is also useful as a solvent for some inorganic salts. In addition, it is also useful as an intermediate in dye stuffs and pharmaceuticals as well as being used in the production of the synthetic material Orlon, said Orlon being a trademark for an acrylic fiber.

It is therefore an object of this invention to provide a process for the production of dialkyl formamides.

A further object of this invention is to provide a process for treating dialkyl amines with carbon dioxide and hyrogen to form the corresponding dialkyl formamides.

In one aspect an embodiment of this invention resides in a process for the preparation of a dialkyl formamide which comprises reacting a dialkyl amine with carbon dioxide and hydrogen in the presence of a transition metal hydrogenation catalyst at reaction conditions, and recovering the resultant dialkyl formamide.

A specific embodiment of this invention is found in a process for the preparation of a dialkyl formamide which comprises reacting dimethylamine with carbon dioxide and hydrogen in the presence of copper chromite at a temperature in the range of from about 100° to about 400° C. and a pressure in the range of from about 5 to about 300 atmospheres, and in the additional presence of potassium carbonate, and recovering the resultant N,N-dimethylformamide.

Other objects and embodiments will be found in the following further detailed description of the present invention.

As hereinbefore set forth the present invention is concerned with a process for the production of dialkyl formamides which involves the treatment of a dialkyl amine with carbon dioxide and hydrogen in the presence of a transition metal hydrogenation catalyst. In addition, if so desired, an alkali metal compound such as an alkali metal hydroxide or alkali metal carbonate would also be present in the reaction mixture, said compound acting as a promoter for the reaction. The treatment of the dialkyl amine with carbon dioxide and hydrogen will be effected at reaction conditions which will include a temperature in the range of from about 100° to about 400° C. and a pressure in the range of from about 5 to about 300 atmospheres. The superatmospheric pressure at which this reaction is operated will result from the presence of the carbon dioxide and hydrogen in the reactor. However, it is also contemplated within the scope of this invention that the carbon dioxide and hydrogen will afford only a partial portion of the desired operating pressure, the remainder of the desired pressure being afforded by the introduction of an inert gas such as nitrogen, argon, helium, etc., along with the carbon dioxide and hydrogen to provide the aforesaid desired operating pressure. In addition to the operating conditions of temperature and pressure, another operating parameter will include the residence time during which the reaction is allowed to be effected. It is contemplated that the reaction will be allowed to proceed for a period of time ranging from about 0.5 up to about 10 hours or more in duration, the particular residence time being dependent upon variable factors which include temperature, pressure, reactants, catalyst, etc.

Examples of dialkyl amines which may be used as the starting material in the process of this invention will include those secondary amines containing from 1 to about 20 carbon atoms or more in the alkyl chain. Some specific examples of these dialkyl amines which may be used will include dimethylamine, diethylamine, di-n-propylamine, diisopropylamine, di-n-butylamine, di-t-butylamine, di-n-pentylamine, di-sec-pentylamine, the isomeric dihexylamines, diheptylamines, dioctylamines, dinonylamines, didecylamines, diundecylamines, didodecylamines, ditridecylamines, ditetradecylamines, dipentadecylamines, dihexadecylamines, diheptadecylamines, dioctadecylamines, dinonadecylamines, eicosylamines.

Examples of transition metal hydrogenation catalysts which may be employed to effect the desired reaction of the present process will include noble metals of Group VIII of the Periodic Table composited on a solid support such as platinum composited on kieselguhr, platinum composited on alumina, platinum composited on silica, platinum composited on carbon, platinum cpmposited on activated carbon, palladium composited on kieselguhr, palladium composited on alumina, palladium composited on silica, palladium composited on carbon, palladium composited on activated carbon, rhodium composited on kieselguhr, rhodium composited on alumina, rhodium composited on slilica, rhodium composited on carbon, rhodium composited on activated carbon, ruthenium composited on kieselguhr, ruthenium composited on alumina, ruthenium composited on silica, ruthenium composited on carbon, ruthenium composited on activated carbon, osmium composited on kieselguhr, osmium composited on alumina, osmium composited on silica, osmium composited on carbon, osmium composited on activated carbon, iridium composited on kieselguhr, iridium composited on alumina, iridium composited on silica, iridium composited on carbon, iridium composited on activated carbon; other metals of Group VIII of the Periodic Table such as Raney nickel, Raney cobalt, nickel composited on kieselguhr, nickel composited on alumina, cobalt composited on kieselguhr, cobalt composited on alumina; other transition metals such as rhenium, rhenium composited on kieselguhr, rhenium composited on alumina, rhenium composited on silica, Raney copper, copper chromite, molybdenum oxide, molybdenum sulfide, cobalt-molybdenum mixed oxide, etc. It is to be understood that the aforementioned transition metal hydrogenation catalysts are only representative of the type of catalyst which may be employed to effect the desired reaction, and that the present invention is not necessarily limited thereto. In addition to the catalysts it is also contemplated within the scope of this invention, if so desired, that an alkali metal compound may also be present in the reaction mixture to act as a promoter for the reaction. Examples of these alkali metal compounds will include alkali metal hydroxides such as lithium hydroxide, sodium hydroxide, potassium hydroxide, rubidium hydroxide, cesium hydroxide, and alkali metal carbonates such as lithium carbonate, sodium carbonate, potassium carbonate, rubidium carbonate, and cesium carbonate.

The process of this invention may be effected in any suitable manner and may comprise either a batch or continuous type operation. For example, when a batch type operation is employed, a quantity of the dialkyl amine which is to be treated is placed in an appropriate apparatus which is pressure resistant such as an autoclave of the rotating, rocking, or mixing variety. In addition, the transition metal hydrogenation catalyst is also placed in the vessel along with the alkali metal hydroxide or alkali metal carbonate, if so desired, and the autoclave is sealed. The autoclave is then brought to the desired operating pressure by introducing a mixture of carbon dioxide and hydrogen, the carbon dioxide being present in the gas mixture in a mole ratio within the range of from about 0.1:1 up to about 1:1 moles of carbon dioxide per mole of hydrogen. Upon attaining the desired operating pressure, the autoclave is then heated to a predetermined operating temperature and maintained thereat for a predetermined period of time within the range hereinbefore set forth. At the end of the desired residence time, heating is discontinued and after the autoclave has returned to room temperature the excess pressure is discharged. The autoclave is opened and the reaction mixture is recovered therefrom. The liquid product is then separated from the catalyst by decantation, filtration, etc., and thereafter subjected to conventional means of separation such as fractional distillation, crystallization, etc., whereby the desired product comprising a dialkyl formamide is separated from any unreacted starting materials and/or any unreacted side products which may have formed during the reaction and recovered.

It is also contemplated within the scope of this invention that the process for obtaining a dialkyl formamide may also be effected in a continuous manner of operation. When this type of operation is employed, the dialkyl amine is continuously charged to a reaction vessel containing the transition metal hydrogenation catalyst and, if so desired, the alkali metal compound while maintaining the vessel at the proper operating conditions of temperature and pressure. As in the case of the batch type operation, the pressure is attained by continuously charging the mixture of carbon dioxide and hydrogen to the reaction vessel. After passage through the reaction vessel for a predetermined period of time, the reactor effluent is continuously withdrawn and subjected to conventional means of separation similar in nature to those hereinbefore set forth whereby the desired dialkyl formamide is separated and recovered while any unreacted starting materials may be recycled to the reaction vessel to form a portion of the feed stock.

The continuous method of operation may be effected in several different ways. For example, one method of effecting the operation is to use a fixed bed operation in which the catalyst is maintained as a fixed bed in the reaction vessel and the dialkyl amine is passed over the catalyst bed in either an upward or downward flow. A second method which may be used comprises a moving bed operation in which the catalyst bed and the reactant are passed through the reaction vessel either concurrently or countercurrently to each other. Alternatively, a slurry type operation may be employed in which the catalyst is carried into the reaction vessel as a slurry in the reactant. Examples of dialkyl formamides which may be prepared according to the process herein described will include N,N-dimethylformamide, N,N-diethylformamide, N,N-di-n-propylformamide, N,N-diisopropylformamide, N,N-di-n-butylformamide, N,N-di-t-butylformamide, the isomeric dipentylformamides, dihexylformamides, diheptylformamides, dioctylformamides, etc.

The following examples are given for purposes of illustrating the process of this invention. However, it is to be understood that these examples are given merely for purposes of illustration, and that said invention is not necessarily limited thereto.

EXAMPLE I

In this example 5.05 grams of copper chromite was placed in an autoclave along with 20.0 grams of dimethylamine. The autoclave was sealed and carbon dioxide and hydrogen charged thereto until an initial operating pressure of 234 atmospheres was reached. The molar ratio of dimethylamine to carbon dioxide to hydrogen in this experiment was 1:1:4.2. The autoclave was then heated to a temperature of 154° C. and maintained thereat for a period of 3 hours, the pressure during this time dropping from 234 atmospheres to 223 atmospheres. At the end of the 3 hour period, heating was discontinued and after the autoclave had returned to room temperature the excess pressure was discharged, the autoclave was then opened and the reaction mixture recovered therefrom. Analysis of the product disclosed a 21.6% yield of N,N-dimethylformamide based on the dimethylamine feed. Selectivity for dimethylformamide was about 100%.

EXAMPLE II

In this example 5.01 grams of a catalyst comprising nickel composited on kieselguhr was placed in an autoclave along with 20.0 grams of dimethylamine. The autoclave was sealed and hydrogen and carbon dioxide charged thereto until an initial operating pressure of 238 atmospheres was reached. The mole ratio of dimethylamine to carbon dioxide to hydrogen was the same as that in Example I above. The autoclave was heated to a temperature of 156° C. and maintained thereat for a period of 3 hours, the pressure during this time dropping from 238 atmospheres to 230 atmospheres. At the end of the 3 hour period heating was discontinued, the autoclave was allowed to return to room temperature, the excess pressure was discharged and the autoclave was opened. After recovery of the reaction product, it was subjected to analysis which determined a 19.4% yield of N,N-dimethylformamide with about 100% selectivity to this product.

EXAMPLE III

This run utilized a catalyst comprising 5% platinum composited on carbon, 1.0 gram of this catalyst along with 10.0 grams of potassium carbonate being charged to an autoclave. In addition, 20.1 grams of dimethylamine was charged to the autoclave which was sealed and pressured with carbon dioxide and hydrogen until an initial operating pressure of 135 atmospheres was reached. Thereafter the autoclave was heated to a temperature of 150° C. and maintained thereat for a period of 3 hours. During the reaction period the pressure dropped from 135 atmospheres to 124 atmospheres. At the end of the residence time, the autoclave and contents thereof were treated in a manner similar to that hereinbefore set forth. Analysis of the reaction product disclosed a 14.8% yield of dimethylformamide with about 100% selectivity.

The above experiment was repeated using 5% platinum composited on carbon as the catalyst but omitting the presence of a promoter. The reaction conditions included an initial operating pressure of 265 atmospheres, an operating temperature of 185° C. and a residence time of 10 hours. In addition the carbon dioxide to hydrogen feed was varied so that the mole ratio of dimethylamine to carbon dioxide to hydrogen was 1:1:3. Analysis of the reaction mixture after recovery from the autoclave disclosed a 11.3% yield of N,N-dimethylformamide with again a selectivity of about 100%.

EXAMPLE IV

In this experiment 1.01 grams of a catalyst comprising 5% palladium composited on charcoal along with 1.30 grams of cesium hydroxide which acted as a promoter were placed in an autoclave along with 20 grams of dimethylamine. The autoclave was sealed and carbon dioxide and hydrogen pressed in until an initial operating pressure of 82 atmospheres was reached. The autoclave was then heated to a temperature of 163° C. and maintained thereat for a period of 3 hours, the pressure during this time rising to 91 atmospheres. At the end of this time the autoclave was treated in a manner similar to that hereinbefore set forth and analysis of the reaction mixture disclosed an 11.2% yield of N,N-dimethylformamide with a selectivity of about 100%.

EXAMPLE V

The catalyst in this run again comprised 1 gram of 5% palladium composited on carbon with a promoter comprising 10 grams of potassium carbonate. 20.0 Grams of dimethylamine was charged to the reactor which was then sealed and pressured to 255 atmospheres by the introduction of carbon dioxide and hydrogen, said carbon dioxide and hydrogen being placed in an amount so that the mole ratio of dimethylamine to carbon dioxide to hydrogen was 1:1:3. After heating the autoclave to a temperature of 176° C. and maintaining the autoclave at this temperature for a period of 10 hours, during which time the operating pressure droped to 246 atmospheres, heating was discontinued and the autoclave allowed to return to room temperature. Again the excess pressure was discharged, the autoclave was opened and the reaction mixture was recovered therefrom. Analysis of this mixture disclosed a 37.2% yield of N,N-dimethylformamide with a selectivity of about 100%.

A repeat of the above experiment using only 1 gram of potassium carbonate, an operating pressure of 113 atmospheres and a temperature of 161° C. for a period of 3 hours with a mole ratio of a dimethylamine to carbon dioxide to hydrogen of 1:1:1 resulted in a 19.7% yield of N,N-dimethylformamide.

EXAMPLE VI

To illustrate the use of a different transition metal hydrogenation catalyst, 1.03 grams of 5% ruthenium composited on carbon was placed in an autoclave along with 1 gram of potassium carbonate as a promoter and 20 grams of dimethylamine. The autoclave was sealed and pressured to 110 atmospheres with carbon dioxide and hydrogen. After heating the autoclave to a temperature of 152° C., it was maintained thereat for a period of 3 hours. At the end of this period the autoclave and contents thereof were treated in a manner similar to that hereinbefore set forth. Analysis of the product disclosed a 10.1% yield of N,N-dimethylformamide.

When the above experiment was repeated using a catalyst comprising 1.01 grams of a 5% rhodium composited on carbon along with 1 gram of potassium carbonate as a promoter, there was obtained an 8.7% yield of N,N-dimethylformamide. Another run in which the potassium carbonate promoter was omitted resulted in only a 0.3% yield of N,N-dimethylformamide.

EXAMPLE VII

When other dialkyl amines such as diethylamine, di-n-butylamine, di-sec-pentylamine and di-n-octylamine may be treated with carbon dioxide and hydrogen in the presence of transition metal hydrogenation catalysts such as nickel composited on keiselguhr using promoters such as sodium hydroxide, potassium carbonate, etc., the reaction product when analyzed, may also show comparable yields of the corresponding N,N-dialkyl formamides such as N,N-diethylformamide, N,N-di-n-butylformamide, N,N-di-sec-pentylformamide, and N,N-di-n-octylformamide.

I claim as my invention:

1. A process for the preparation of dialkyl formamide which comprises reacting dialkyl amine with carbon dioxide and hydrogen in the presence of a transition metal hydrogenation catalyst and a promoter comprising an alkali metal hydroxide or alkali metal carbonate, and recovering the resultant dialkyl formamide.

2. The process as set forth in claim 1 in which the reaction conditions include a temperature in the range of from about 100° to about 400° C. and a pressure in the range of from about 50 to about 300 atmospheres.

3. The process as set forth in claim 1 in which said transition metal hydrogenation catalyst comprises copper chromite.

4. The process as set forth in claim 1 in which said transition metal hydrogenation catalyst comprises nickel composited on kieselguhr.

5. The process as set forth in claim 1 in which said transition metal hydrogenation catalyst comprises palladium composited on carbon.

6. The process as set forth in claim 1 in which said transition metal hydrogenation catalyst comprises platinum composited on carbon.

7. The process as set forth in claim 1 in which said transition metal hydrogenation catalyst comprises ruthenium composited on carbon.

8. The process as set forth in claim 1 in which said promoter comprises potassium carbonate.

9. The process as set forth in claim 1 in which said promoter comprises cesium hydroxide.

10. The process as set forth in claim 1 in which said promoter comprises sodium hydroxide.

11. The process as set forth in claim 1 in which said dialkyl amine is dimethylamine and said dialkyl formamide is N,N-dimethylformamide.

12. The process as set forth in claim 1 in which said dialkyl amine is diethylamine and said dialkyl formamide is N,N-diethylformamide.

13. The process as set forth in claim 1 in which said dialkyl amine is di-n-butylamine and said dialkyl formamide is N,N-di-n-butylformamide.

14. The process as set forth in claim 1 in which said dialkyl amine is di-sec-pentylamine and said dialkyl formamide is N,N-di-sec-pentylformamide.

15. The process as set forth in claim 1 in which said dialkyl amine is di-n-octylamine and said dialkyl formamide is N,N-di-n-octylforamide.

* * * * *